United States Patent [19]

Guirguis

[11] Patent Number: 5,077,012
[45] Date of Patent: Dec. 31, 1991

[54] DEVICE FOR DETECTING DISEASE MARKERS

[75] Inventor: Raouf A. Guirguis, Rockville, Md.

[73] Assignee: La Mina Ltd., British Virgin Isls.

[21] Appl. No.: 506,070

[22] Filed: Apr. 9, 1990

Related U.S. Application Data

[63] Continuation-in-part of Ser. No. 308,763, Jan. 10, 1989, Pat. No. 4,961,432, and a continuation-in-part of Ser. No. 440,117, Nov. 22, 1989, Pat. No. 5,022,411.

[51] Int. Cl.$^5$ ............................................. G01N 21/00
[52] U.S. Cl. ....................................... 422/58; 422/55; 436/63; 436/165; 128/760; 604/317
[58] Field of Search ............... 422/58, 57, 55; 436/63, 436/165; 128/760; 604/317

[56] References Cited

U.S. PATENT DOCUMENTS 4,960,130 10/1990 Guirguis ............................. 128/760

FOREIGN PATENT DOCUMENTS 9000251 1/1990 European Pat. Off. ............. 422/58

Primary Examiner—Robert J. Warden
Assistant Examiner—Laura E. Collins
Attorney, Agent, or Firm—John S. Hale

[57] ABSTRACT

An apparatus for collecting biological fluids and holding samples taken from a biological fluid for qualitative and quantitative testing. The apparatus comprises a tubular container open at both ends with a quantitative test storage unit removably secured to one of said tubular container ends. The quantitative test storage unit has an open end, a cytology membrane mounted in the storage unit and a retaining rib. A shuttle assembly is slidably mounted in the tubular container comprising a cylindrical hollow piston defining a chamber, a thumb cover covering one end of the piston and a fluid flow aperture formed in the piston and a qualitative sample container assembly removable secured to the piston. The qualitative sample container assembly comprises a clip on membrane assembly including a membrane containing immobilized antibodies and a filter housing mounted to the clip on membrane asssembly. The filter housing is adapted to be seated in the quantitative test storage unit after being slidably transported along the tubular container by the piston.

26 Claims, 8 Drawing Sheets

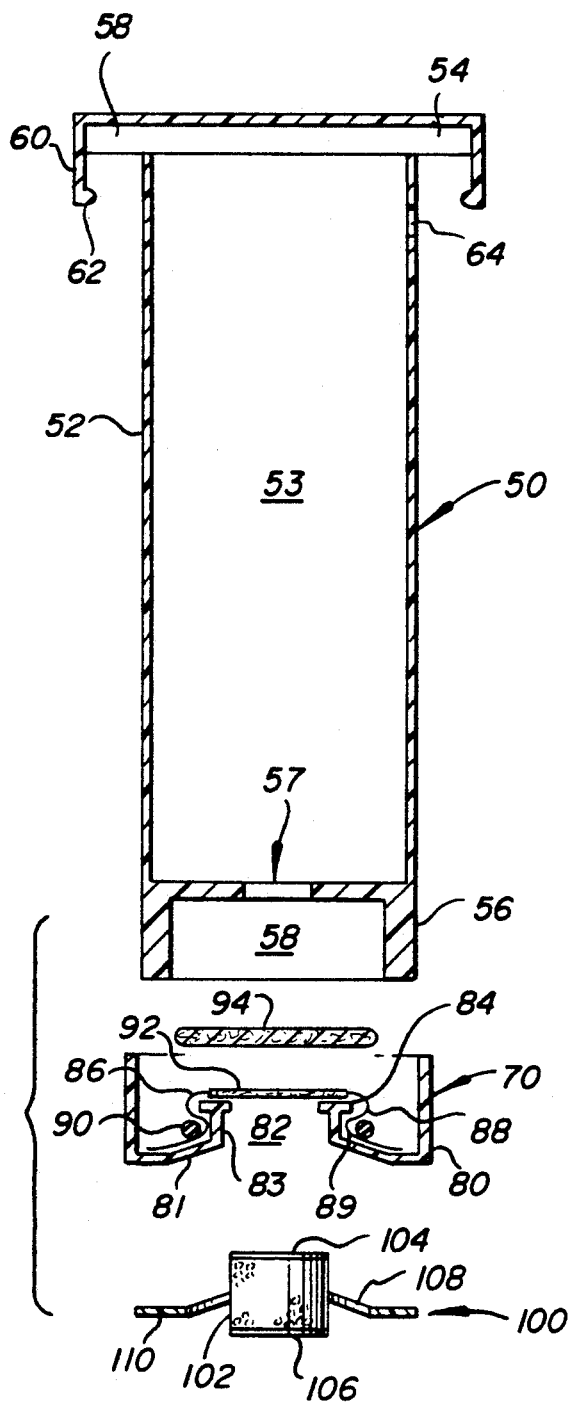
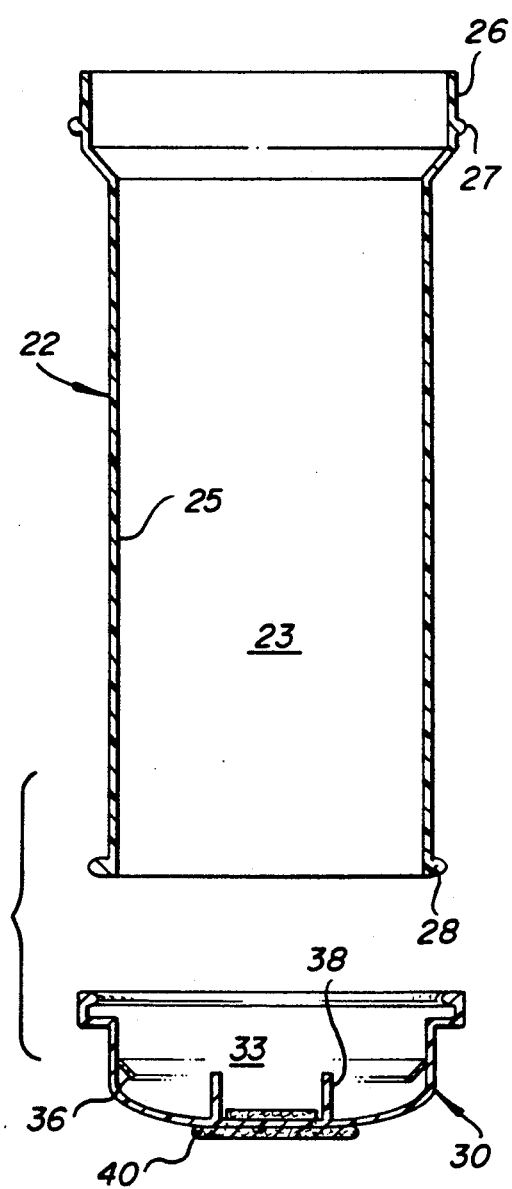

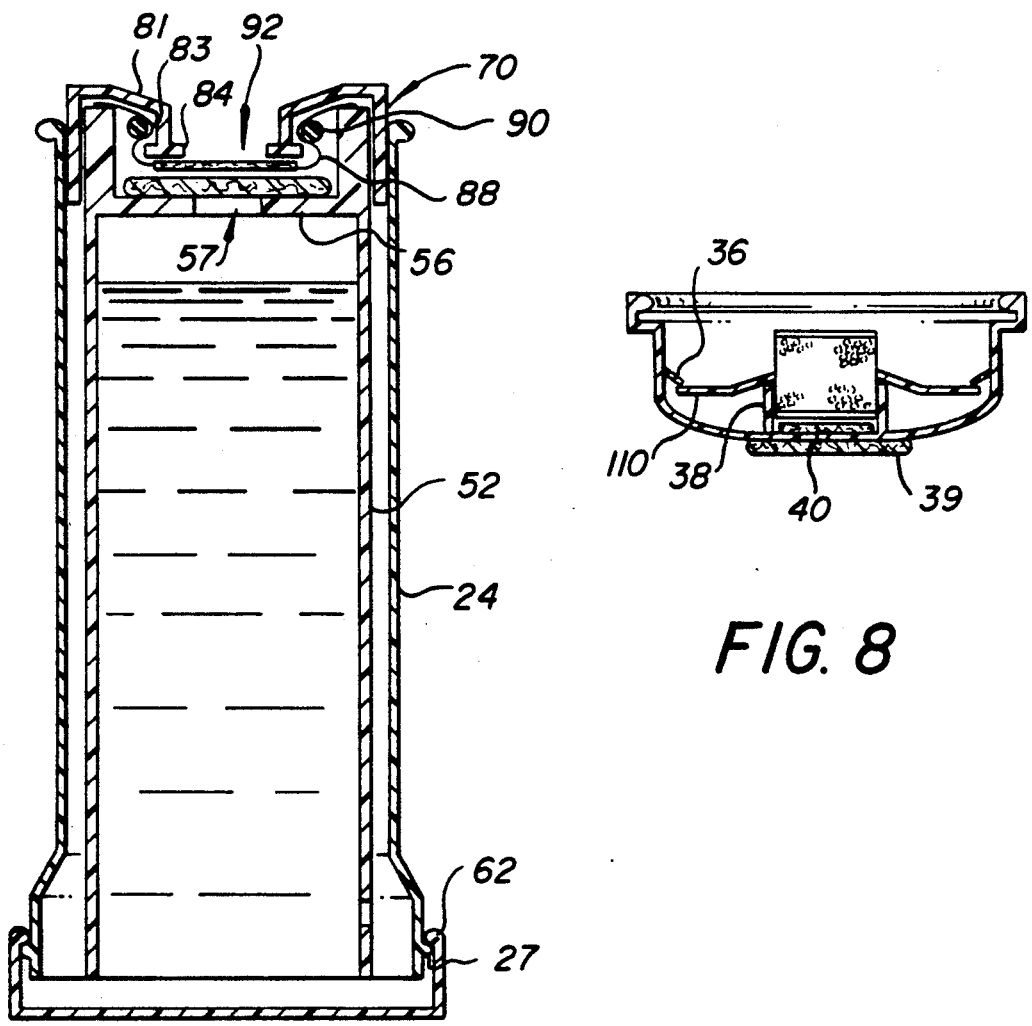

DEVICE FOR DETECTING DISEASE MARKERS

RELATED CASES

This is a continuation-in-part application of U.S. patent application Ser. No. 07/308,763 filed Jan. 10, 1989 now U.S. Pat. No. 4,961,432 and U.S. patent application Ser. No. 07/440,117 filed Nov. 22, 1989 now U.S. Pat. No. 5,022,411.

BACKGROUND OF THE INVENTION

1. Field of the Invention

The present invention is directed to medical and laboratory specimen collecting and testing equipment, and more specifically to an apparatus for detecting disease markers both for screening as well as for a reference laboratory setting.

2. Description of the Prior Art

It is generally necessary in diagnosing and testing for many diseases to collect biological fluids from a patient, e.g., sputum, blood, pleural and peritoneal cavity fluids, urine, etc. for analysis. It is important during the collection handling of biological fluid specimens that the potential of specimen contamination and the spread of any infection from the specimen be minimized. In addition there is also the potential for specimen damage during the collection and/or shipment process as well as the potential for destruction of certain components of the specimen because the packaging collects and holds different fluid components which will negate the test results or result in false data being obtained when the specimen is tested.

One of the problems in collecting biological fluid specimens and testing and collecting specific disease markers from the fluid specimens occurs not only during the collection of the specimens but also in the transport or shipment of the specimens after collection to the laboratory for analysis.

A typical specimen collecting apparatus is shown by U.S. Pat. No. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial which in connection with the cap allows the user to remove the vial without touching the surface or coming in contact with the specimen. Examples of various types of liquid containers for collecting and transporting urine are shown by U.S. Pat. Nos. 3,777,739; 3,881,465; 4,042,337; 4,084,937; 4,244,920; 4,492,258 and 4,700,714.

One such specimen collection device shown by U.S. Pat. No. 4,040,791 discloses a collection receptacle having a nipple upon which is mounted a specimen container which receives a predetermined amount of the specimen in a sealed condition. The specimen container is provided with an integrally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 and is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

The use of cytology cups and membranes is known in the art. The Nuclepore Schisto-Kit ™ is designed for rapid and accurate quantification of Schistosome eggs in urine by the membrane filtration technique. A simple syringe filtration permits collection of virtually all eggs onto the smooth flat surface of a transparent Nuclepore polycarbonate membrane filter. Quantitative egg counts without staining are easily made with a low power magnifier. Other cytology cups are marketed under the trademark SWIN-LOK and Swinnex Disc Filter Holder.

Nuclepore polycarbonate membranes are used for diagnostic cytology. The surface allows collection of atypical cells from all types of body fluids.

It is therefore desirable to provide an easy to handle apparatus which obtains body fluid samples such as blood or urine with a minimum chance for spillage and contamination between collection and laboratory as well as a need to separate various biological components of the body fluid. In addition, cells contained in the fluid have a valuable medical use so that capturing the same for further testing is beneficial. In using the present invention testing can be performed quickly and accurately with minimum time.

For some testing, particularly where antigens are being removed from the body fluids for a variety of tests, it is desirable to remove the antigens from the fluid so that various test procedures can be run. It is also desirable to do so with minimal exposure of laboratory personnel to the sample subject of testing. Previously this has been accomplished by a series of tests involving a number of different containers and expensive laboratory equipment. Mass testing using such a series of tests is expensive, time consuming, and often unsatisfactory.

SUMMARY OF THE INVENTION

There is provided in the practice of the invention, according to the presently preferred embodiment, a body fluid collection and testing device. This device is in the form of a tubular device having a removable cytology cup which contains a prefiltration/beads housing and cytology membrane for quantitative analysis and a transportable syringe in the housing with a coloration membrane for qualitative test analysis. A capture antibody is immobilized on the membrane surface of the syringe head which is in contact with the body fluid. After the body fluid sample is processed, the prefilteration/beads housing becomes part of the cytology cup leaving the syringe head with membrane exposed. The cytology cup is then detached from the syringe body and the syringe body is inverted upside down to add the coloring reagents to the membrane.

If the screening test is positive (qualitative) for the disease marker, the bead housing and the cytology cup will be sent to the reference laboratory for further analysis (quantitative).

In the accompanying drawings, there is shown an illustrative embodiment of the invention from which these and other of objectives, novel features and advantages will be readily apparent.

BRIEF DESCRIPTION OF THE DRAWINGS

FIG. 2 is an exploded cross sectional view of the piston assembly and test assembly which fits into the cytology cup of FIG. 1;

FIG. 3 is a cross sectional view of exploded parts of the tubular collection assembly and cytology cup;

FIG. 7 is an inverted cross sectional view of the collection tube and piston assembly, collection tube and membrane testing module positioned for the membrane screening test;

FIG. 8 is a cross sectional view of the separated cytology cup assembly of FIG. 6;

DETAILED DESCRIPTION OF THE INVENTION

The preferred embodiment and best mode of the invention is seen in FIGS. 1 through 11. The invention shown therein comprises a modular separable body fluid testing device. While the invention can be used for any body fluid such as sputum, blood, peritoneal cavity fluid, pleural cavity fluid or urine, it is primarily designed for use in collecting urine/blood samples for use in testing for the presence of various kinds of disease markers, such as cancer in the body.

Figure 1:
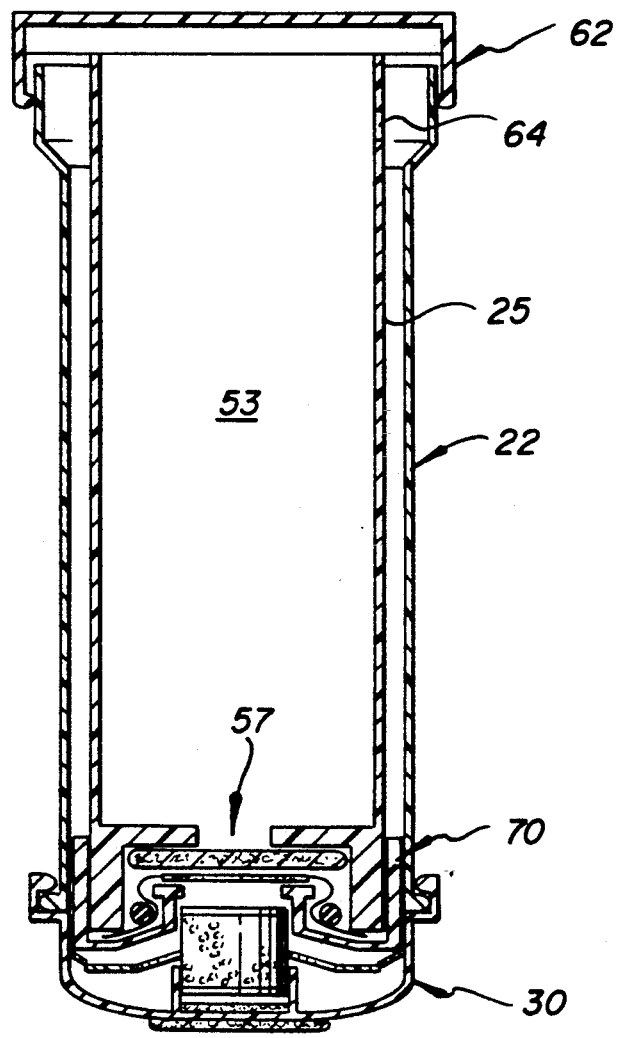
FIG. 1 is a cross sectional view of the assembled inventive membrane shuttle and cytology cup apparatus.
Figure 4:
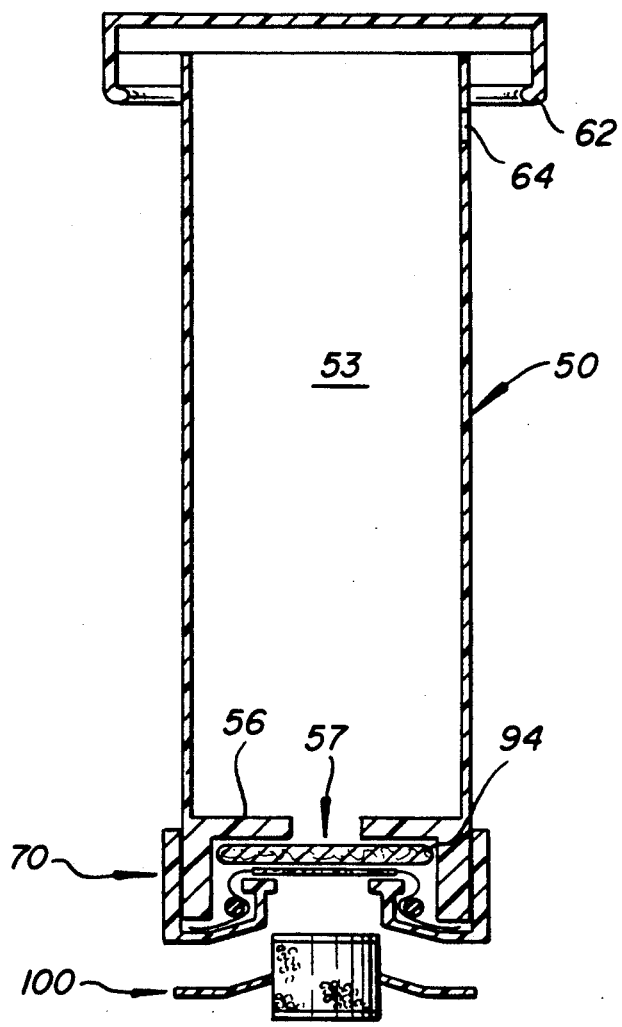
FIG. 4 is an exploded cross sectional piston assembly and prefilteration bead housing unit.

As shown in FIGS. 1–3, a sample testing apparatus 20 is constructed of polystyrene and comprises a tubular collection unit or syringe barrel 22, a cytology cup 30 and a piston 50 with associated piston head test assembly 70.

The tubular collection unit or syringe barrel 22 is constructed with a tubular open ended cylindrical body 24 defining a chamber 23 with an open flared end portion 26 and circular locking rib 27 formed on one end and on the other end a circular locking rib 28. The flared end portion 26 has a wide mouth to more easily receive body fluid such as urine or blood which is loaded into the chamber. It should be noted that a prelabelled antibody is added to the body fluid sample along with the buffer reagents.

A cytology cup 30 is removably secured to the body 24 by virtue of a snap on fit of the cups locking mechanism over the rib 28. The cytology cup 30 comprises a cylindrical cup shaped body 32 with a locking lip mechanism comprising a stepped portion 33 and a flexible lip member 34 ending in rib 35. The lip rib 35 has an inner lesser diameter than the outer diameter of rib 28, allowing rib 28 to be snap fit into the locking lip mechanism.

A downwardly extending circular flange member 36 extends inwardly toward the chamber of the cup to hold a bead housing assembly 100 in place in the cytology cup 30. The cytology cup is also provided with a cytology membrane housing comprised of a cylindrical barrel body 38 and an end member 39. The cytology membrane housing is removably mounted or secured in an aperture formed in the bottom surface of the body 32 with the barrel 38 extending upward into the chamber and the end member seated adjacent the bottom surface of the cytology cup 30. The barrel 38 holds a cytology membrane 40 which is seated on end member 39 at the bottom of the cup where cells can be captured at the end of the assay. The preferred membrane 40 which is used is manufactured by Nuclepore and can be cut in discs ranging from 13 mm to 293 mm in diameter with a pore size of 2.0 um or less and exhibits a tensile strength of over 3000 psi. The prefered material composition is polycarbonate although polyester can be used. The membrane is flexible and will not crack and is resistent to splitting or breakage. These membrane filters have a pore size, pore density and pore structure which are geometrically defined and photomicrographs of the same reveal individual pore openings on the surface with diameters closely equal to the rated pore size of the membrane. The advantages of a defined surface pore size are the complete surface capture of all particulate larger than the rated pore size, excellent particulate visibility and internal reference scale for particulate sizing.

The smooth flat surface of the membrane offers an ideal substrate for particulate analysis using either optical or electron microscopy. Those membranes with pore size larger than 1.0 um are sufficiently transparent to permit transmitted light allowing viewing of objects on the membrane surface without cleaning the membrane. The membrane can be coated with a hydrophilic surface that yields nearly instantanous flash-wetting with aqueous solutions. Such membranes when coated are coated with polyvinylphrrolidone (PVP) to render them hydrophilic. However the membrane can be PVP free if so desired.

Figure 6:
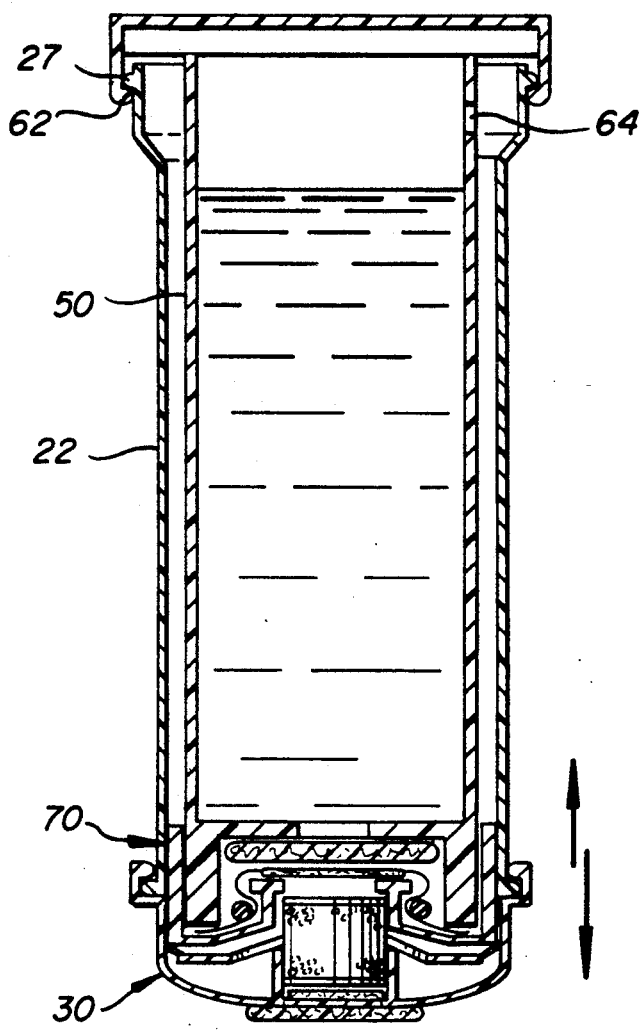
FIG. 6 is a cross sectional view of the assembly after the body fluid has been processed.

Thus the cytology diagnostic membrane 40 has a smooth flat surface which is ideal for the collection of atypical cells from all types of body fluids. Polycarbonate membranes are semi-transparent permitting direct microscopy or may easily be dissolved to remove all pore image artifacts. Thus the advantages which occur in the use of a polycarbonate membrane are minimum clogging by red blood cells and protein, well preserved cellular morphology with high recovery rate, rapid filtration with low pressure, and excellent surface capture due to the pore structure and porosity. The smooth flat surface permits high cell visibility, improved morphologic resolution and surface capture. The membrane thickness allows easy mounting and immediate microscopic examination. The membranes low absorption and adsoption provides improved contrast, greater cell isolation and easy mounting while its non-staining characteristics allow improved contrast and simpler microscopic analysis. Furthermore the chemical resistance of the membrane is unaffected by conventional cytologic fixatives and stains. The barrel also serves as a holder for the bead housing assembly as shown in FIG. 6.

A piston 50 as shown in FIG. 2 is designed to fit within cylindrical body of the syringe barrel 24 and slideably move along the interior wall surface 25 holding a test assembly 70 for deposit within the cytology cup. The piston 50 is constructed of a transparent plastic and comprises a hollow cylindrical piston body 52 provided with a thumb cover assembly 54 and a cross sectional U-shaped bottom end member 56 of thicker construction than the piston body 52. The thumb cover assembly 54 includes a thumb support member 58 with a downwardly projecting flexible skirt or flange 60 ending in locking rib 62. The locking rib 62 is adapted to lock onto syringe rib 27 as the rib 62 cams the flange 60 so that it springs outward allowing rib 62 to ride over rib 27 and then snap back into place thereby securing the piston 50 on the syringe barrel 22. An air release aperture 64 is formed in the piston body so that there is communication between the interior chamber 53 of the piston body into the outside atmosphere. The bottom endwall 56 is provided with a throughgoing aperture 57 which allows communication with the chamber 53.

Figure 5:
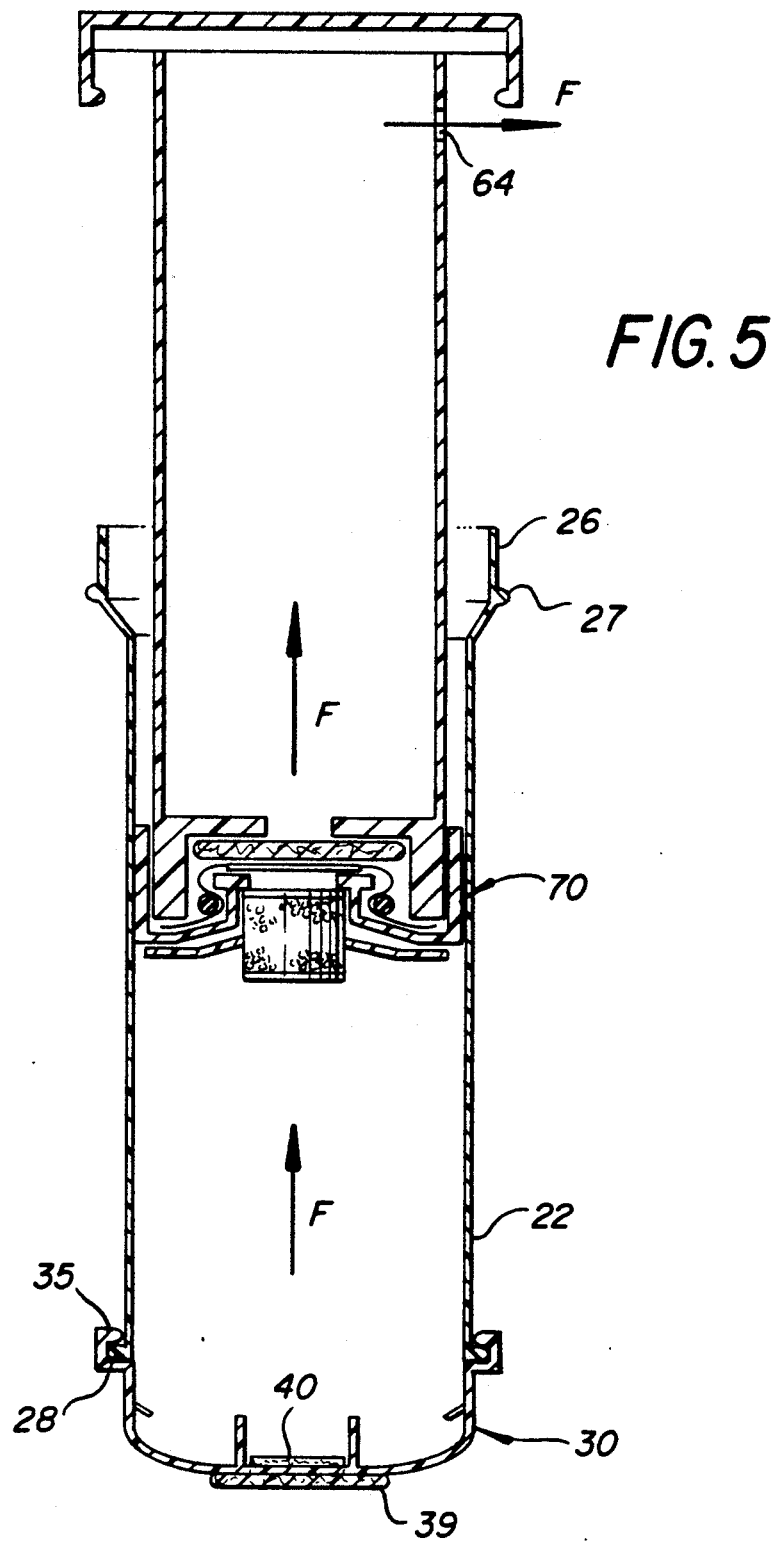
FIG. 5 is a cross sectional view of the assembled membrane shuttle and cytology cup apparatus with direction of movement of the fluid being shown by arrows F.

The test assembly 70 as shown in exploded parts in FIG. 2 is constructed with a cylindrical base cap shaped member having an interior diameter equal to or slightly less than the exterior diameter of endwall 56 so that it can be friction fit on same and a funnel shaped endwall 81 which funnels into a cylindrical section 83 which serves as a chamber for housing body 102 and a support for seat 84. The endwall by virtue of section 83 is provided with a pass through port or opening 82. The port 82 is further defined by a circular ring shaped membrane disk seat 84 which sits over the port. The seat 84 is provided with a flat upper surface to hold membrane 92 and a flat lower surface 85 forming a stop for the body 102 of the bead housing assembly. A membrane clip assembly 86 with a plastic cup body 87 and curved spring skirt 88 is mounted over the disc seat 84 and curls back under the disc seat 84 toward cylindrical section 83 forming a circular channel 89 and then extends outward along the inner surface 81 of the base member body 80 to provide a tight fit for attachment of the membrane clip assembly to the rim of the disc seat 84. An elastomeric "O" ring 90 abuts the surface of the skirt 88 in channel 89 to hold the membrane clip assembly tightly on the disc seat and the membrane 92 positioned over port 82. The plastic membrane member 92 is provided with immobilized ligands preferably in the form of antibodies and is seated on disc seat 84 over port 82. A porous support disc member 94 provides support for membrane 92 against the fluid flow comming through port 82 and sits in the endwall cavity 58 over port 57 so that the fluid pressure will not rupture the membrane 92. Thus the disc support member 94 sits in the cavity 58 of bottom end member 56 as is shown in FIGS. 5 and 6. Opposite the membrane member 92 on the opposite side of the disc seat 84, a prefilteration bead housing assembly 100 is seated in cavity 82 formed by cylindrical section 83 against the back of disc seat 84 which as noted operates as a stop. All of the parts of the membrane clip assembly are preferably integrally molded in one piece.

The bead housing assembly 100 is constructed with a barrel shaped cylindrical body 102 open at both ends and threaded to allow the mounting of circular top cover 104 and bottom cover 106 which are threadably mounted on the inside of the cylindrical body. These endwalls are provided with throughgoing perforations or apertures or are formed with porous septums to allow easy flowthrough of fluids. A saucer shaped housing support member 108 with a flat rim 110 is contoured to fit around the outer surface of cylindrical body 102 and keeps the bead housing from contacting cytology cup. The membrane 40 while locking the bead housing in the chamber of the cytology cup under rib 36. While the bead housing is preferably used for prefilteration of the body fluids used for screening and cytology it alternately can be filled with resin material to collect antigen for quantitative studies. In this regard, bead housing body 102 may be filled with resin/sample consisting of beads of all forms and sizes which can be specifically manufactured for ion exchange (e.g., fast flow Q-sepharose anion exchange, and Fast Flow S-sepharose cation exchange from Pharmacia), high affinity chromatography or hydrophobicity (e.g., phenylsepharose beads). Preferably, the module holds high affinity resin with specific antibodies immobilized onto the solid phase resin (e.g., protein A, etc.) so that antigens in the sample can bind to their specific antibodies while passing through the resin module and become immobilized as well.

It should be noted that the air contained in chamber 53 is pushed out by the fluid entering through port 57 into chamber 53 through air release aperture 64 into a chamber formed by the concentric outer surface of the piston body 52 and the inner surface 25 of syringe barrel 22. The test assembly 70 is pushed down by the piston body until it enters into the body cavity 33 of the cytology cup 30 past the spring rib 36. At this time the lower surface of the rim 110 of bead housing support 108 engages and deflects the spring rib 36 thus seating the bead housing 100 in a predetermined position held in the cytology cup. The body fluid entering the body chamber 53 through port 57 will be trapped inside it even after removal of the cytology cup 30 as shown in FIG. 7.

Figure 10A:
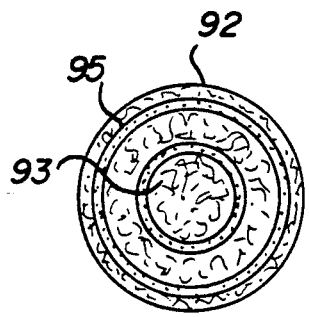
FIGS. 10(a); 10(b) and 10(c) are top plan views of the testing membrane shown in FIG. 9 showing positive, negative and bad reagent test results.
Figure 10B:
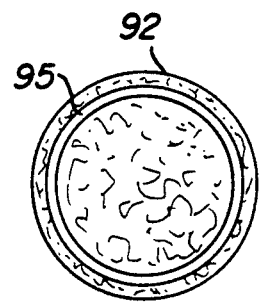
Figure 10C:
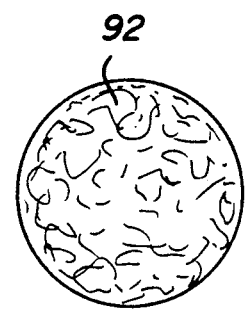
Figure 11:
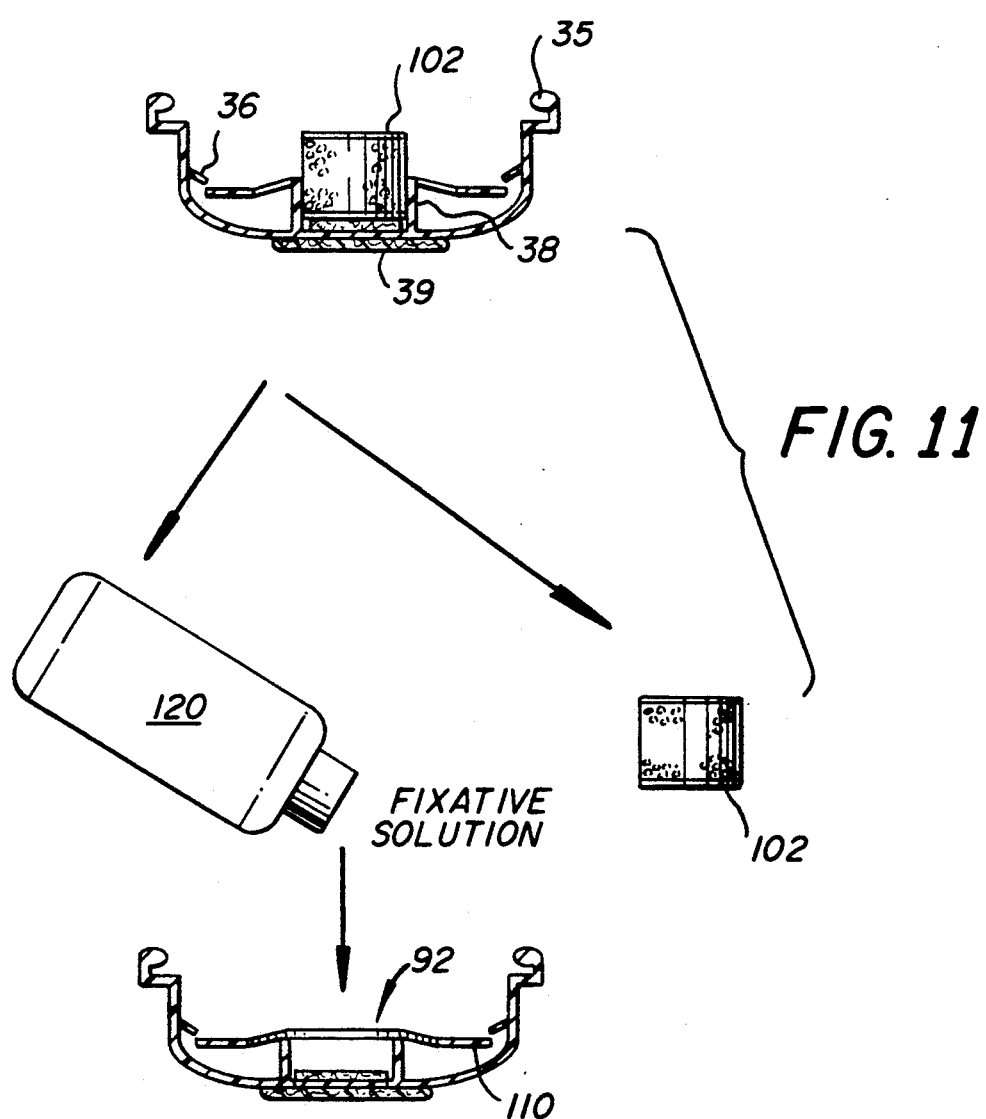
FIG. 11 is an exploded cross sectional view of the bead housing removed from the cytology cup and fixative solution being added to the cytology membrane.

The membrane surface 92 is provided with immobilized antibodies which having had flow contact with the bodily fluid captures the specific component of the fluid which is to be tested; in this example, antigens caused by cancer cells. The cytology cup 30 is then pulled off of the syringe barrel 22 with the bead housing 100 contained therein. The piston 50 remains with the syringe barrel 22, and test assembly 70 so when the same is inverted membrane 92 can be tested with a color developing solution as seen in FIGS. 10(a)-(c).

The body fluid which will be placed in compartments 23 and 33 (see FIGS. 6-8) contains lyophilized primary labelled antibodies having a binding site contoured to the epitope structure and chemistry of an antigen. This antigen has been previously determined as being a marker for a specific type of disease, preferably cancer. The antibodies are labelled with HRP (horseradish peroxidase), an enzyme that detoxifies hydrogen peroxide, $H_2O_2$, by converting it to water. HRP initiates this transformation when it gives hydrogen peroxide a pair of electrons. The enzyme subsequently collects these electrons from suitable donors. Thus the total color generated by peroxidase depends upon the relative rates of color generation and product inactivation of the enzyme. Membrane 92 contains antibodies immobilized (covalently bound) thereto in area 93 for reception of the complexed antibodies and is provided with a second area 95 which acts as a control. The antigen has epitopes which have a high affinity for the binding sites of the primary labelled antibody and immobilized antibody. The principle of affinity chromatography requires that a successful separation of a biospecific ligand is available and that it can be chemically immobilized to a chromatographic bed material, the matrix. Numbers of methods well known in the art have been used to couple or immobilize the antibodies to a variety of matrixes. Examples of immobilization techniques which exhibit variable linkage are those formed by the reaction of the reactive groups on the support with amino, thiol, hydroxyl, and carboxyl groups on the protein ligand. The selection of the ligand is influenced by two factors. First, the ligand should exhibit specific and reversible binding affinity for the substance to be purified and secondly it should have chemically modifiable groups which allow it to be attached to the matrix without destroying its binding activity. (Examples of such are Protein G Sepharose manufactured by Pharmacia, Hydrazide AvidGel Ax manufactured by BioProbe International, and Actigel-ALD manufactured by Sterogene Bioseparation Inc.)

An advantage to the use of Actigel-ALD is that it does not cross link proteins therefore allowing proteins to retain high bioactivity after their immobilization. Actigel-ALO SUPER FLOW, also available from Sterogene Bioseparation Inc., permits a linear flow rate of up to 3000 cm/h which would fit nicely with the flow rates in the apparatus.

After the body fluid, blood/urine mixed with prelabelled antigen has passed over the membrane 92 and deposited complexed ligands on the immobilized antibodies the membrane 92 is preferably soaked with ABTS solution 120 to determine the presence of the disease marker. A hydrogen peroxide ($H_2O_2$) solution may be alternately placed on the membrane when OPD or TMB or other dual substrate systems are used.

The color solution 120 used on the membrane 92 is preferably a substrate manufactured by Kirkegaard & Perry Labs under one of several acronyms namely: ABTS (2,2'-azinodi-[3-ethylbenzthiazoline sulfonate (6)]; OPD (orthophenylene diamine); or TMB (tetramethylkbenzidine). In choosing the substrate, the sensitivity of the immunoassay is determined by the discrimination of the antibody reagents. When this occurs, the use of a more sensitive substrate serves only to proportionately increase the signal and the background. The result is more color but the same signal-to-noise ratio. Should the more sensitive substrate push the absorbance over the cut-off of the reader, the faster substrate may in fact reduce the signal-to-noise ratio.

Figure 9:
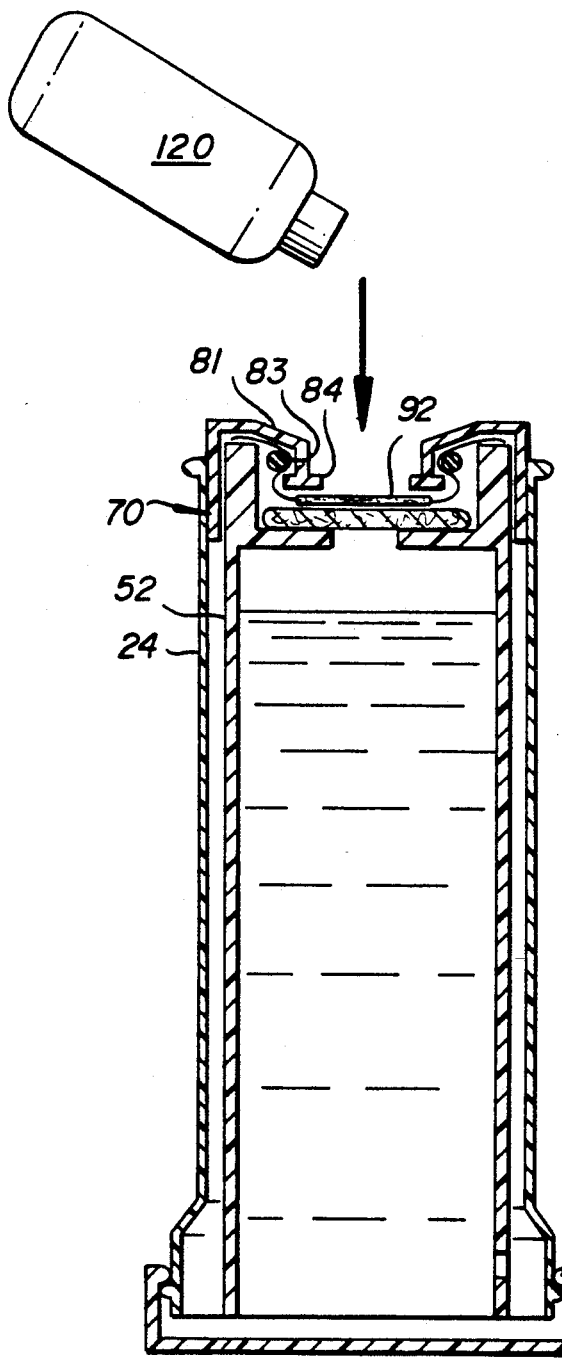
FIG. 9 is a cross sectional view of the apparatus shown in FIG. 7 showing color developing solution being added to the testing membrane.

The preferred color solution 120 as shown in FIG. 9 of the present invention is ABTS. The preferred ABTS substrate is a one-component substrate. The HRP label on the primary antibody is turned by the ABTS to a blue-green color and there is no change in color or absorbance when the reaction is stopped with SDS (sodium dodecyl sulfate). If the assay optimization indicates the sensitivity of the immunoassay is limited by the color generated by the HRP substrate, then the more sensitive TMB substrate would give more color development without a corresponding increase in the background. Another advantage of the TMB substrate is that it often lowers the amount of antibody and antigen reagents required for the immunoassay. TMB substrate is a two component liquid substrate and requires hydrogen peroxide. HRP converts TMB to a blue product. When the reaction is stopped by acidification, the TMB product becomes yellow. ODP is generally provided as a tablet that is dissolved in buffer at the time of use. HRP converts OPD to a yellow product which continues to oxidize into a brown precipitate. Upon acidification the OPD product becomes orange.

The membrane material 92 with matrix and immobilized ligand (in this case immobilized antibody) having had flow contact with the fluid, captures or immobilizes the antibody through antigen-antibody reaction or immune reaction the specific ligand component carried by the fluid, namely, the complexed primary labelled antibody and antigen which was formerly contained by the body fluid in chambers 23 and 33. This antibody as previously noted was provided prelabelled with coloring enzyme HRP. When the specific antigen is present in the testing sample which is added to the container, the antigen reacts with the antibody to form antigen-antibody complexes. This labelling enzyme of the antibody reacts with the ABTS poured on the membrane surface 92 turning the surface of the membrane 93 into a blue green color. If there is an absence of the antigen in the specimen sample, the antibody will remain unoccupied and will not bind to the immobilized antibodies. On the other hand, if the antigen is present, antigen-antibody complexes will be formed and held on the membrane surface for reaction with the ABTS solution. The degree of color developed should correlate with the amount of prelabelled antibody/antigen complexes which in turn correlates with the amount of antigen present in the sample. The positive control area 93 reflects the current state of the coloring reagents as well as the prelabelled antibody at the time the test is performed.

In the foregoing description, the invention has been described with reference to a particular preferred embodiment, although it is to be understood that specific details shown are merely illustrative, and the invention may be carried out in other ways without departing from the true spirit and scope of the following claims.

What is claimed is:

1. An apparatus for testing biological fluids and/or particulate matter comprising a fluid container, a specimen test assembly moveably mounted in said fluid container, said specimen test assembly comprising piston means with a membrane provided with immobilized antibodies and cytology means including a cytology membrane for capturing a biological mass for quantitative analysis, said piston means membrane with immobilized antibodies capturing a predetermined antigen mass for qualitative analysis.

2. An apparatus for testing biological fluids and/or particulate matter comprising a fluid container with removable cytology cup means, a specimen test assembly moveably mounted in said fluid container, said specimen test assembly comprising piston means, a membrane assembly mounted in said piston means, said membrane assembly including a membrane means provided with immobilized antibodies selected to capture a predetermined antigen mass and a housing means removably mounted to said membrane assembly, said housing means comprising a housing containing fluid filter means.

3. An apparatus for testing biological fluids and/or particulate matter as claimed in claim 2, wherein said fluid container comprises a syringe barrel and said cytology cup means is removably mounted to one end of said syringe barrel.

4. An apparatus for testing biological fluids and/or particulate matter as claimed in claim 3, wherein said cytology cup means is provided with fluid container holding means and housing means for a cytology membrane.

5. An apparatus for testing biological fluids as and/or particulate matter claimed in claim 4, wherein said cup housing means comprises an open ended barrel with a cap removably seated in an aperture defined by said cytology cup means with the open end of the barrel extending into a chamber defined by said cytology cup means.

6. An apparatus for testing biological fluids and/or particulate matter as claimed in claim 2, wherein said housing means comprises a cylindrical housing, a flange means mounted to said housing and extending outward from said cylindrical housing and end members covering both ends of said cylindrical housing, said end members allowing fluid flow therethrough.

7. An apparatus for testing biological fluids and/or particulate matter as claimed in claim 2 wherein said housing means holds beads provided with immobilized antibodies.

8. An apparatus for testing biological fluids and/or particulate matter as claimed in claim 2 wherein said housing means holds a filtration membrane.

9. An apparatus for testing biological fluids and/or particulate matter as claimed in claim 6, wherein said flange means comprises a saucer shaped member extending outward from the outer surface of said cylindrical barrel.

10. An apparatus for testing biological fluids and/or particulate matter as claimed in claim 9, wherein said saucer shaped member has a flat rim and defines fluid flow means allowing fluid flow therethrough.

11. An apparatus for testing biological fluids and/or particulate matter as claimed in claim 2, wherein said piston means comprises a piston barrel defining a chamber, a cap member mounted over one end of said piston barrel and an end support means formed on the other end of said piston barrel, said end support means defining an aperture therein allowing fluid flow into said barrel chamber.

12. An apparatus for testing biological fluids and/or particulate matter as claimed in claim 2, wherein a prelabelled antibody is added to a body fluid sample held in said fluid container.

13. An apparatus for testing biological fluids and/or particulate matter as claimed in claim 12, wherein buffer reagents are added to said body fluid sample along with said prelabelled antibody held in said fluid container.

14. An apparatus for testing biological fluids and/or particulate matter as claimed in claim 5, wherein a cytology membrane is seated at the bottom of the barrel on t he barrel cap to capture cells at the end of the assay.

15. An apparatus for testing biological fluids and/or particulate matter as claimed in claim 2 wherein said housing means holds beads provided with immobilized antibodies.

16. An apparatus for testing biological fluids and/or particulate matter as claimed in claim 2 wherein said membrane is polycarbonate with a pore size of 2.0 um or less.

17. An apparatus for testing biological fluids and/or particulate matter as claimed in claim 2 wherein said membrane is coated with a hydrophilic surface.

18. An apparatus for collecting biological fluids and holding samples taken from a biological fluid for testing comprising a tubular container open at both ends, a quantitative test storage unit removably secured to one of said tubular container ends, said quantitative test storage unit having an open end, a cytology membrane mounted in said storage unit and retaining means defined by said storage unit, a shuttle assembly slidably mounted in said tubular container, said shuttle assembly comprising a cylindrical hollow piston, defining a chamber, a cover means covering one end of said piston and fluid flow means formed in said piston and a qualitative sample container means removably secured to said piston, said qualitative sample container means comprising a clip on membrane assembly including a membrane containing immobilized antibodies and filter housing means mounted to said clip on membrane assembly, said filter housing means being adapted to be seated in said quantitative test storage unit after being slidably transported along said tubular container by said piston.

19. An apparatus for collecting biological fluids and holding a biological sample for testing comprising an open ended tubular container; a cytology cup means removably secured to one of said tubular container ends to form a closed container which can hold biological fluid, said cytology cup means comprising a body, cytology membrane holding means mounted to said body, a membrane held by said cytology membrane holding means and locking means secured to said body, said locking means being adapted to lock onto one end of said tubular container, a shuttle assembly slidably mounted in said tubular container, said shuttle assembly comprising a cylindrical hollow piston defining a chamber with fluid flow means and a testing means removably mounted to said piston, said testing means comprising a housing provided with means to allow fluid flow therethrough and sample holding membrane means removably mounted to said housing, said sample holding means capturing biological specimens from the biological fluid flowing through the testing means housing by the action of the shuttle assembly moving in the tubular container.

20. An apparatus for collecting biological fluids and holding a biological sample for quantitative and qualitative testing comprising a container having open ends; a cytology cup removably secured to one end of said container, said cytology cup being provided with a stop rib and a cytology membrane, a piston assembly slidably mounted in said open ended container, said piston assembly comprising a hollow piston body with an internal surface defining a chamber, fluid flow means formed in said piston body providing fluid communication with said chamber, a cap member covering one end of said piston, said cap member being provided with locking means allowing it to be locked on to said container, fluid sample ligand capture means removably secured to said piston body, said ligand capture means comprising a cylindrical housing with one end defining an aperture allowing body fluid flow therethrough to contact a membrane with immobilized ligands, said ligand capture means being adapted to visually indicate the presence of specific biological components on designated areas of a membrane surface.

21. An apparatus for collecting biological fluid and removing a biological sample from the fluid for quantitative and qualitative testing as claimed in claim 20 wherein said fluid sample ligand capture means includes a filter housing mounted to said cylindrical housing and filter means seated in said filter housing to filter out predetermined sized biological components carried by the biological fluid and prevent said predetermined sized components from contacting the biological sample capture means membrane.

22. An apparatus as claimed in claim 20 wherein said biological fluid is urine.

23. An apparatus as claimed in claim 20 wherein said biological fluid is blood.

24. An apparatus as claimed in claim 20 wherein said biological fluid sample capture means comprises a polycarbonate membrane with a pore size of 2.0 um of less.

25. An apparatus for testing biological fluids and particulate matter comprising a fluid container with removable cytology cup means, a specimen test assembly moveably mounted in said fluid container, said specimen test assembly comprising piston means, a membrane assembly mounted in said piston means, said membrane assembly comprising a cup shaped housing with a funnel shaped end wall defining an aperture therein and seat means surrounding said aperture, a membrane means is mounted to said housing and seated on said seat means covering said aperture, said membrane means being provided with immobilized antibodies selected to capture a predetermined antigen mass and a housing means removably mounted to said membrane assembly, said housing means comprising a housing containing fluid filter means.

26. An apparatus for testing biological fluids and/or particulate matter as claimed in claim 25, wherein said membrane means comprises a curved spring loaded plastic clip member defining a channel and constructed to engage said cup shaped housing, a membrane provided with immobilized antibodies is mounted on said spring loaded plastic clip member and an "O" ring is mounted on said spring loaded plastic clip member in said channel holding said membrane means on said cup shaped housing.

* * * * *